(12) United States Patent
    Soerensen

(10) Patent No.: US 11,103,640 B2
(45) Date of Patent: Aug. 31, 2021

(54) DRUG DELIVERY DEVICE WITH FRONT LOADING FEATURE

(71) Applicant: Novo Nordisk A/S, Bagsvaerd (DK)

(72) Inventor: Morten Soerensen, Ballerup (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 14/379,943

(22) PCT Filed: Jan. 25, 2013

(86) PCT No.: PCT/EP2013/051452
§ 371 (c)(1),
(2) Date: Aug. 20, 2014

(87) PCT Pub. No.: WO2013/124118
PCT Pub. Date: Aug. 29, 2013

(65) Prior Publication Data
US 2015/0335825 A1    Nov. 26, 2015

Related U.S. Application Data

(60) Provisional application No. 61/604,883, filed on Feb. 29, 2012, provisional application No. 61/636,768, filed on Apr. 23, 2012.

(30) Foreign Application Priority Data

Feb. 24, 2012  (EP) ..................................... 12156902
Apr. 17, 2012  (EP) ..................................... 12164439

(51) Int. Cl.
*A61M 5/24*      (2006.01)
*A61M 5/315*     (2006.01)

(52) U.S. Cl.
CPC ............ *A61M 5/24* (2013.01); *A61M 5/3158* (2013.01); *A61M 5/31548* (2013.01);
(Continued)

(58) Field of Classification Search
CPC ................ A61M 5/14546; A61M 5/24; A61M 5/31525; A61M 5/31551;
(Continued)

(56) References Cited

U.S. PATENT DOCUMENTS 2,531,893 A    11/1950  Roehr
2,646,798 A    7/1953   Brown
(Continued)

FOREIGN PATENT DOCUMENTS

EP    0829268        3/1998
EP    0937474 A2     8/1999
(Continued)

*Primary Examiner* — Bhisma Mehta
*Assistant Examiner* — James D Ponton
(74) *Attorney, Agent, or Firm* — Wesley Nicolas

(57) ABSTRACT

A drug delivery device adapted to receive a cartridge and hold it in a mounted position is provided, comprising a housing, an expelling assembly, and a front-loaded cartridge holder assembly adapted to receive and hold a cartridge in a mounted state. The assembly comprises cartridge holding means actuatable between a receiving state and a holding state, as well as a user operated actuation sleeve being rotationally actuatable relative to the housing between a loading state and an operational state, such that the cartridge holding means is actuated from the receiving state to the holding state when the actuation sleeve is actuated from the loading state to the operational state. The actuation sleeve is configured to enclose at least a portion of a mounted cartridge and is provided with inspection means allowing at least a portion of an enclosed cartridge portion to be visually inspected.

9 Claims, 3 Drawing Sheets

(52) U.S. Cl.
CPC ............... *A61M 2005/2411* (2013.01); *A61M 2005/2437* (2013.01); *A61M 2005/2477* (2013.01); *Y10T 29/49876* (2015.01)

(58) Field of Classification Search
CPC .. A61M 2005/2411; A61M 2005/2433; A61M 2005/2437; A61M 2005/2477; A61M 2005/2481; A61M 2005/2485–2496
See application file for complete search history.

(56) References Cited

U.S. PATENT DOCUMENTS

| | | | |
|---|---|---|---|
| 2,778,359 | A | 1/1957 | Friedman |
| 3,114,178 | A | 12/1963 | Wood |
| 3,115,135 | A | 12/1963 | Sarnoff |
| 3,144,178 | A | 8/1964 | Sarnoff et al. |
| 3,380,452 | A | 4/1968 | Elias |
| 3,437,090 | A | 4/1969 | Sarnoff |
| 3,976,069 | A | 8/1976 | Ong |
| 4,585,445 | A | 4/1986 | Hadtke |
| 4,624,660 | A | 11/1986 | Mijers et al. |
| 4,808,169 | A | 2/1989 | Haber et al. |
| 4,990,142 | A | 2/1991 | Hoffman et al. |
| 5,002,537 | A * | 3/1991 | Hoffman ............... A61M 5/24 604/232 |
| 5,078,698 | A | 1/1992 | Stiehl et al. |
| 5,549,575 | A | 8/1996 | Giambattista et al. |
| 5,989,226 | A | 11/1999 | Hymanson |
| 6,042,571 | A | 3/2000 | Hjertman et al. |
| 6,159,184 | A | 12/2000 | Perez et al. |
| 6,277,097 | B1 * | 8/2001 | Mikkelsen ............... A61M 5/24 604/187 |
| 6,582,399 | B1 | 6/2003 | Smith et al. |
| 6,585,698 | B1 | 7/2003 | Packman et al. |
| 6,648,859 | B2 | 11/2003 | Bitdinger et al. |
| 6,899,699 | B2 | 5/2005 | Enggaard |
| 7,762,994 | B2 | 7/2010 | Klint et al. |
| 8,267,900 | B2 | 9/2012 | Harms et al. |
| 8,579,868 | B2 | 11/2013 | Christiansen |
| 8,613,731 | B2 | 12/2013 | Hansen et al. |
| 8,632,506 | B2 | 1/2014 | Steenfeldt-Jensen et al. |
| 8,672,897 | B2 | 3/2014 | Elahi et al. |
| 8,740,857 | B2 | 6/2014 | Christiansen et al. |
| 9,050,397 | B2 | 6/2015 | Christiansen |
| 2003/0109834 | A2 | 6/2003 | Bitdinger et al. |
| 2004/0108339 | A1 | 6/2004 | Hansen et al. |
| 2004/0199117 | A1 | 10/2004 | Giambattista et al. |
| 2004/0210199 | A1 | 10/2004 | Atterbury et al. |
| 2005/0277896 | A1 | 12/2005 | Messerli et al. |
| 2006/0089593 | A1 | 4/2006 | Landau et al. |
| 2007/0073232 | A1 | 3/2007 | Pickhard |
| 2008/0097338 | A1 | 4/2008 | Cheng et al. |
| 2009/0118669 | A1 | 5/2009 | Bendek et al. |
| 2009/0275914 | A1 | 11/2009 | Harms et al. |
| 2011/0046566 | A1 | 2/2011 | Elahi et al. |
| 2011/0092917 | A1 | 4/2011 | Wei et al. |
| 2011/0152822 | A1 | 6/2011 | Drunk et al. |
| 2012/0172812 | A1 | 7/2012 | Plumptre et al. |
| 2013/0211327 | A1 | 8/2013 | Osman et al. |
| 2013/0220869 | A1 | 8/2013 | Klintenstedt et al. |
| 2013/0226082 | A1 | 8/2013 | Klintenstedt et al. |
| 2013/0253432 | A1 | 9/2013 | Avery et al. |
| 2013/0253433 | A1 | 9/2013 | Senior et al. |
| 2013/0289488 | A1 | 10/2013 | Riess et al. |
| 2014/0358093 | A1 | 12/2014 | Soerensen et al. |
| 2015/0011949 | A1 | 1/2015 | Soerensen |
| 2015/0335825 | A1 | 11/2015 | Soerensen |

FOREIGN PATENT DOCUMENTS

| | | |
|---|---|---|
| EP | 2460552 A1 | 6/2012 |
| JP | H1099434 A | 4/1998 |
| JP | 2002509469 A | 3/2002 |
| WO | 00/02605 A1 | 1/2000 |
| WO | 2004020026 A1 | 3/2004 |
| WO | 2004020036 A2 | 3/2004 |
| WO | 2004047895 A1 | 6/2004 |
| WO | 2007104636 A1 | 9/2007 |
| WO | 2007134954 A1 | 11/2007 |
| WO | 2008062025 A1 | 5/2008 |
| WO | 2010066796 A1 | 6/2010 |
| WO | 2010097116 A1 | 9/2010 |
| WO | 2011039216 A2 | 4/2011 |
| WO | 2011039227 A2 | 4/2011 |
| WO | 2011039228 A1 | 4/2011 |
| WO | 2011045385 A1 | 4/2011 |
| WO | 11051366 A2 | 5/2011 |
| WO | 2011051366 A2 | 5/2011 |
| WO | 2011053225 A1 | 5/2011 |
| WO | 11067269 A1 | 6/2011 |
| WO | 2011089207 A2 | 7/2011 |
| WO | 2011092326 A1 | 8/2011 |
| WO | 2011124631 A1 | 10/2011 |
| WO | 2011124632 A1 | 10/2011 |
| WO | 2011131776 A1 | 10/2011 |
| WO | 2011131779 A1 | 10/2011 |
| WO | 2012085017 A2 | 6/2012 |
| WO | 2012130704 A1 | 10/2012 |
| WO | 2012152667 A1 | 11/2012 |

* cited by examiner

DRUG DELIVERY DEVICE WITH FRONT LOADING FEATURE

CROSS-REFERENCE TO RELATED APPLICATIONS

This application is a 35 U.S.C. § 371 National Stage application of International Application PCT/EP2013/051452 (published as WO 2013/124118), filed Jan. 25, 2013, which claimed priority of European Patent Application 12156902.4, filed Feb. 24, 2012 and European Patent Application 12164439.7, filed Apr. 17, 2012; this application claims priority under 35 U.S.C. § 119 of U.S. Provisional Application 61/604,883, filed Feb. 29, 2012 and U.S. Provisional Application 61/636,768, filed Apr. 23, 2012.

DRUG DELIVERY DEVICE WITH FRONT LOADING FEATURE

The present invention generally relates to drug delivery devices adapted to receive a drug filled cartridge and expel a dose therefrom.

BACKGROUND OF THE INVENTION

In the disclosure of the present invention reference is mostly made to the treatment of diabetes, however, this is only an exemplary use of the present invention.

The most common type of injection devices adapted to receive a drug filled cartridge and expel a dose therefrom are generally pen-formed and utilizes a so-called cartridge holder adapted to receive and mount a cartridge in the device. Correspondingly, most pen-formed drug delivery devices comprises a generally cylindrical cartridge holder for receiving and holding a generally cylindrical drug-filled cartridge in a mounted position, the cartridge comprising a proximally facing and axially displaceable piston, and a main body with a housing in which a drug expelling mechanism is arranged, the mechanism comprising an axially displaceable piston rod adapted to engage the piston of a mounted cartridge to thereby expel a dose of drug from the cartridge. Between the cartridge holder and the main body a connection means is provided allowing a user to remove the cartridge holder from the main body and reattach it when a used cartridge has been exchanged with a new cartridge. The cartridge is in most cases inserted in the cartridge holder by axial movement through a proximal opening, see e.g. WO 2011/124631, EP 0 937 474 and WO 2011/092326. The connection means may be in the form of a threaded connection or a bayonet coupling. Depending on the design of the drug delivery device the piston rod has to be moved proximally (i.e. "reset") by rotation when an empty cartridge is exchanged with a full cartridge, or the piston rod can be reset by being pushed axially, e.g. by unlocking the piston rod when the cartridge holder is removed from the main body, this as disclosed in for example US 2009/0275914 and WO 2011/051366.

Alternatively, the drug delivery device may comprise an integrated (i.e. for the user nonremovable) cartridge holder adapted to axially receive a cartridge through a distal opening. Such a device is often named "front loaded", see e.g. WO 2004/020026. The cartridge holder may be provided with gripping means adapted to hold and release an axially inserted cartridge.

Having regard to the above, it is an object of the present invention to provide a drug delivery device adapted to receive a drug-filled cartridge in a simple and effective way, the arrangement being to a high degree user-friendly, reliable as well as cost-effective.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in accordance with a first aspect of the invention a drug delivery is provided which is adapted to receive a cartridge and hold it in a mounted position, the cartridge comprising a cylindrical body portion, a distal outlet portion and an axially displaceable piston. The drug delivery device comprises a housing and an expelling assembly comprising a piston rod adapted to engage and axially displace a piston in a mounted cartridge in a distal direction to thereby expel a dose of drug from the cartridge, and a drive assembly adapted to move the piston rod in the distal direction corresponding to a set dose. The drug delivery device further comprises a front-loaded cartridge holder assembly having a central axis and being adapted to receive and hold a cartridge in a mounted state, the assembly comprising cartridge holding means actuatable between a receiving state in which a cartridge can be received in a proximal direction, and a holding state in which a received cartridge is held in an operational mounted position, as well as a user operated actuation sleeve being rotationally actuatable relative to the housing between a loading state and an operational state, wherein the cartridge holder is actuated from the receiving state to the holding state when the actuation sleeve is actuated from the loading state to the operational state. The actuation sleeve is configured to enclose at least a portion of a mounted cartridge (or otherwise worded: enclose at least a portion of the space adapted to receive and hold a cartridge), the actuation sleeve comprising inspection means allowing at least a portion of an enclosed cartridge portion to be visually inspected. In this way an easy-to-use front loaded drug delivery device can be provided which may appear as a traditional rear loaded device and which is also actuated by rotational movement to mount and remove a cartridge, the resemblance providing for ease of acceptance and adaptation among users accustomed to traditional types of rear loaded drug delivery devices. In an exemplary embodiment wherein the actuation sleeve encloses the distal portion of the cartridge holding means in the operational state.

The cartridge holding means may comprise one or more distal gripping portions, e.g. two opposed portions, which are moved towards the central axis when the cartridge holding means is actuated from the receiving state to the holding state, and which are moved away from the central axis when the cartridge holding means is actuated from the holding state to the receiving state.

In an exemplary embodiment the cartridge holding means comprises one or more locking arms, e.g. two opposed arms, each having one of the distal gripping portions, this allowing an arrangement in which each locking arm is moved proximally when the cartridge holder is actuated from the receiving state to the holding state, and each locking arm is moved distally when the cartridge holder is actuated from the holding state to the receiving state. The actuation sleeve and the locking arms may be operationally coupled to each other such that each locking arm is moved laterally and held in a lateral receiving position when the locking arm is moved distally corresponding to the receiving state, and each locking arm is moved centrally and held in a central holding position when the locking arm is moved proximally corresponding to the operational state.

Depending on the given design of the cartridge holding means, a given locking arm may comprise one or more openings or be at least partially transparent. Correspondingly, the actuation sleeve may comprise one or more openings or be at least partially transparent, thereby providing the inspection means.

In exemplary embodiments the cartridge holding means is rotationally coupled to the actuation means, either rotationally locked or providing a gearing. When the cartridge holding means and the actuation sleeve is rotationally locked to each other the cartridge holding means and the actuation sleeve may be provided with inspection openings in moving alignment with each other as the actuation sleeve is rotated.

The expelling assembly may further comprise a coupling mechanism actuatable between a resetting state in which the piston rod can be moved proximally, and an operational state in which the drive assembly can drive the piston rod distally but in which the piston rod cannot be moved proximally, wherein the coupling is actuated from the resetting state to the operational state when the actuation sleeve is actuated from the loading state to the operational state. In such an arrangement the actuation sleeve may be actuatable from a loading state through an intermediate state to an operational state, wherein the cartridge holder is actuated from the receiving state to the holding state when the actuation sleeve is actuated from the loading state to the intermediate state, and the coupling is actuated from the resetting state to the operational state when the actuation sleeve is actuated from the intermediate state to the operational state.

Any of the above-described drug delivery devices may be provided in combination with a cartridge comprising a cylindrical body portion, a distal outlet portion and an axially displaceable piston, the cartridge being adapted to be received in and hold in the mounted position in the cartridge holder assembly. The actuation sleeve may axially enclose at least 50% of the length of a mounted cartridge (or otherwise worded: enclose at least 50% of the length of the space adapted to receive and hold a cartridge), for example 75% or 90%. As the proximal-most portion of a cartridge may be received in the distal portion of the housing and thus proximally of the actuation sleeve per se, and as the distal-most portion of the cartridge normally will be in the form of a distal outlet portion protruding from the cartridge holding assembly, the actuation sleeve will normally not enclose the full length of the cartridge.

Correspondingly, in a second aspect of the invention a drug delivery device adapted to receive a cartridge and hold it in a mounted position, the cartridge comprising a cylindrical body portion, a distal outlet portion and an axially displaceable piston, is provided. The drug delivery device comprises a main portion comprising an expelling assembly, and a front-loaded cartridge holder assembly adapted to receive and hold a cartridge in a mounted state. The cartridge holder assembly comprises cartridge holding means actuatable between a receiving state in which a cartridge can be received in a proximal direction, and a holding state in which a received cartridge is held in an operational mounted position, as well as a user operated actuation member being rotationally actuatable relative to the main portion between a loading state and an operational state, wherein the cartridge holding means is actuated from the receiving state to the holding state when the actuation member is actuated from the loading state to the operational state, and wherein the actuation member substantially encloses the cylindrical body portion of a mounted cartridge. To allow visual inspection of a mounted cartridge the actuation sleeve may comprise inspection means allowing at least a portion of the enclosed cartridge portion to be visually inspected. In addition, the drug delivery in accordance with the second aspect may comprise the further features described above.

In a further aspect a method of operating a drug delivery system is provided, comprising the steps of (i) providing a cartridge comprising a cylindrical body portion having opposed distal and proximal portions, a distal outlet portion and an axially displaceable piston, (ii) providing a drug delivery device comprising a front-loaded cartridge holder adapted to axially receive the cartridge in a proximal direction and hold the cartridge in a loaded position, the cartridge holder being actuatable between a receiving and a holding state, an actuation sleeve comprising inspection means, and an expelling assembly adapted to engage and axially displace the piston in a loaded cartridge, (iii) inserting a cartridge in the cartridge holder, the actuation sleeve axially enclosing at least 50% of the cartridge length, and (iv) rotating the actuation sleeve to actuate the cartridge holder from the receiving to the holding state. The method may comprise the further step of inspecting the inserted cartridge through the actuation sleeve inspection means. Otherwise the provided drug delivery in accordance with the method may comprise the further features described above.

As used herein, the term "drug" is meant to encompass any flowable medicine formulation capable of being passed through a delivery means such as a cannula or hollow needle in a controlled manner, such as a liquid, solution, gel or fine suspension, and containing one or more drug agents. The drug may be a single drug compound or a premixed or co-formulated multiple drug compounds drug agent from a single reservoir. Representative drugs include pharmaceuticals such as peptides (e.g. insulins, insulin containing drugs, GLP-1 containing drugs as well as derivatives thereof), proteins, and hormones, biologically derived or active agents, hormonal and gene based agents, nutritional formulas and other substances in both solid (dispensed) or liquid form. In the description of the exemplary embodiments reference will be made to the use of insulin and GLP-1 containing drugs, this including analogues thereof as well as combinations with one or more other drugs.

BRIEF DESCRIPTION OF THE DRAWINGS

In the following the invention will be further described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not to an actual situation of use. The shown figures are schematic representations for which reason the configuration of the different structures as well as their relative dimensions are intended to serve illustrative purposes only.

Figure 1A:
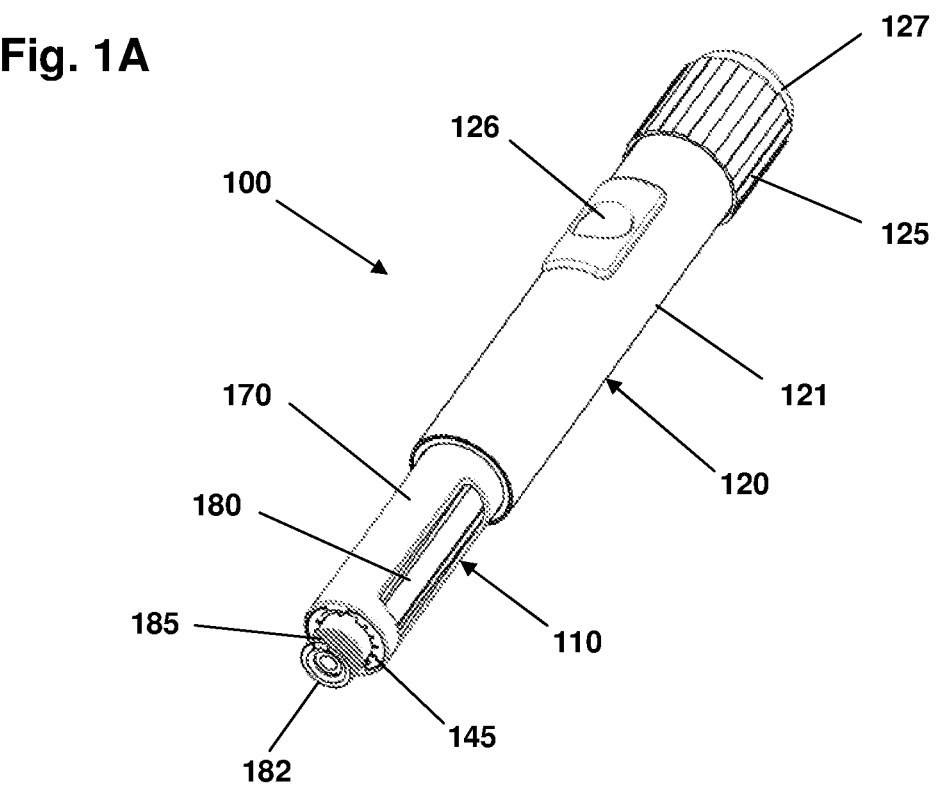
FIGS. 1A and 1B show a front-loaded drug delivery device with respectively without a drug cartridge mounted.

Referring to FIG. 1 a pen-formed drug delivery device 100 will be described. More specifically, the pen device comprises a cap part (not shown) and a main part having a proximal body or drive assembly portion 120 with a housing 121 in which a drug expelling mechanism is arranged or integrated, and a distal cartridge holder portion in which a drug-filled transparent cartridge 180 with a distal needle-penetrable septum 181 is arranged and retained in place by a cartridge holder assembly 110 attached to the proximal portion. The cartridge may for example contain an insulin, a GLP-1 or a growth hormone formulation. The device is designed to be loaded by the user with a new cartridge through a distal receiving opening in the cartridge holder assembly, the cartridge being provided with a piston driven by a piston rod 128 forming part of the expelling mechanism. A proximal-most rotatable dose ring member 125 serves to manually set a desired dose of drug shown in display window 126 and which can then be expelled when the release button 127 is actuated. Depending on the type of expelling mechanism embodied in the drug delivery device, the expelling mechanism may comprise a spring which is strained during dose setting and then released to drive the piston rod when the release button is actuated. Alternatively the expelling mechanism may be fully manual in which case the dose ring member and the release button moves proximally during dose setting corresponding to the set dose size, and then moved distally by the user to expel the set dose. The cartridge is provided with distal coupling means in the form of a needle hub mount 182 having, in the shown example, an external thread 185 adapted to engage an inner thread of a corresponding hub of a needle assembly. In alternative embodiments the thread may be combined with or replaced by other connection means, e.g. a bayonet coupling. The shown exemplary hub mount further comprises a circumferential flange with a number of distally facing pointed projections serving as a coupling means for the cartridge holder assembly as will be described in more detail below. A hub mount of the shown type is described in U.S. Pat. No. 5,693,027.

Figure 2A:
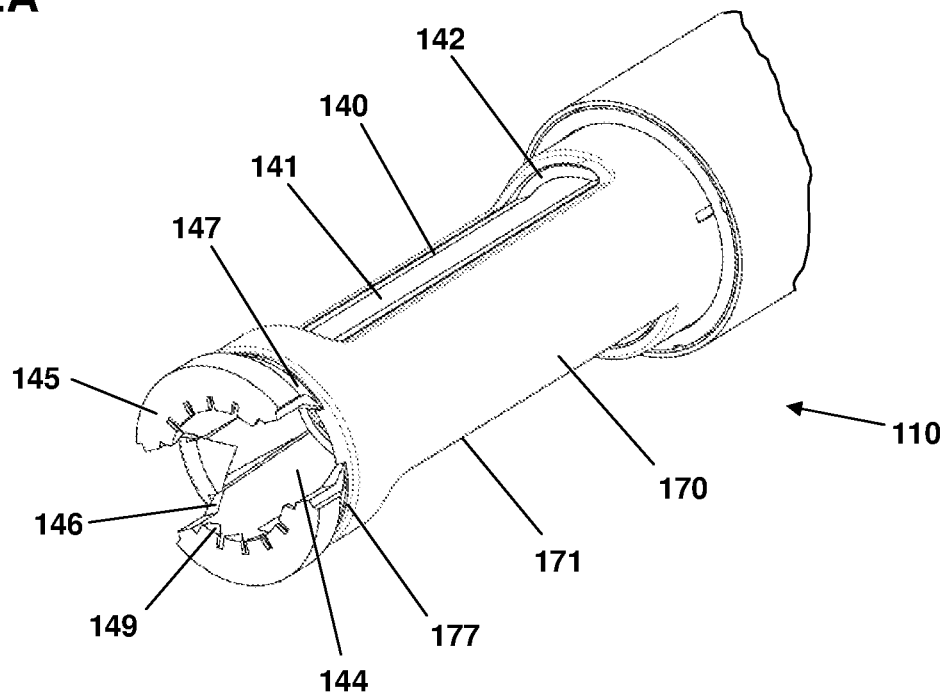
FIGS. 2A and 2B show detail views of the cartridge holder of FIG. 1A in an open respectively closed state.

As shown, the cartridge holder assembly 110 has the same general appearance as a traditional cartridge holder which is detachably coupled to the housing by e.g. a threaded coupling or a bayonet coupling and into which a new cartridge can be received as well as removed through a proximal opening, i.e. it comprises no additional user operated release or locking means. Instead, what appears merely to be the cartridge holder per se is in fact user operated coupling means in the form of an outer rotatable tube member 170 operated by the user to control movement of cartridge holding means in the form of an inner gripping member 140 (see FIG. 2A) to thereby open and close gripping shoulders 145 configured to grip and hold a cartridge. More specifically, the gripping shoulder 145 is provided with a plurality of gripping teeth 149 spaced circumferentially to provide a plurality of gaps, each tooth having a triangular configuration with a proximally oriented pointed end, thereby creating a plurality of gaps having a distally oriented pointed configuration, this allowing the above-described distally facing pointed projections on the cartridge to be received between the teeth 149 to thereby serve as a gripping means when the cartridge holding means has been moved into engagement with the cartridge. In this way an easy-to-use front loaded drug delivery device is provided which appears as a traditional rear loaded device and which is also actuated by rotational movement to mount and remove a cartridge, the resemblance providing for ease of acceptance and adaptation among users accustomed to traditional types of rear loaded drug delivery devices.

Depending on the actual design of a given drug delivery device, the actuation sleeve may fully or partly enclose the cylindrical body portion of a mounted cartridge, or otherwise worded: fully or partly enclose the space adapted to receive and hold the cartridge which may be defined as the space between the piston rod in its proximal-most position and the distal end of the cartridge holder assembly. Correspondingly, the actuation sleeve comprises inspection means allowing at least a portion of an enclosed cartridge portion to be visually inspected. In the shown embodiment the actuation sleeve comprises a pair of opposed longitudinal openings 171. Alternatively or in addition, the actuation sleeve may be formed at least partially from a transparent material. Depending on the design of the actuated cartridge holding means also these may be provided with inspection means in the form of openings and/or transparent portions, see below.

Figure 1B:
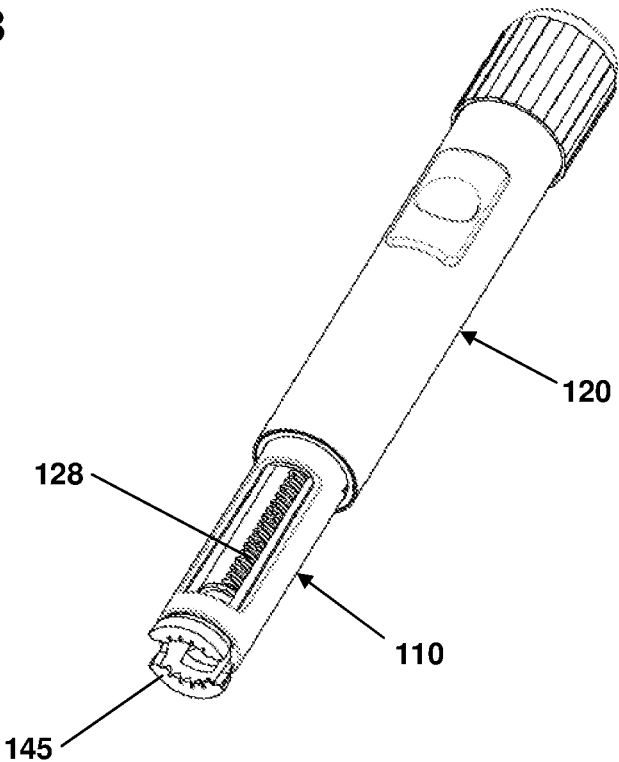

When it is time to mount a new cartridge the outer tube member is rotated e.g. 15 degrees by which action the gripping shoulders 145 are moved distally and slightly outwards, this allowing the mounted cartridge to be removed. For ease of operation the cartridge may be moved distally a certain distance as the shoulders are moved, e.g. by engagement with arms forming the gripping shoulders and/or by additional spring means providing a biasing distally directed force. FIG. 1B shows the device with the cartridge removed and the gripping shoulders in their un-locked "open" position in which a cartridge can be removed and a new inserted.

Depending on the design of the locking and actuation mechanism the gripping shoulders may be able to be left in the open position or they may be retracted automatically as the outer tube member is rotated backwards by return spring means. Whether or not a spring is provided the cartridge holder may be provided with locking means allowing the outer tube member may to be securely parked in either the open or closed position, e.g. by a rotational snap lock.

The mechanical arrangement providing the above-described user-interface, i.e. rotation of an outer tubular sleeve member moves gripping shoulders in and out, can be provided in numerous ways. In the shown embodiment the cartridge gripping member 140 comprises two opposed flexible arms 144 extending from a proximal ring portion 142 arranged in axially guided sliding and thus non-rotational engagement with the outer tubular sleeve member, each arm being provided with a gripping shoulder 145. By this arrangement the gripping shoulders will rotate together with the outer tubular sleeve member and thus relative to the housing 121 as they are moved axially. In shown embodiment two opposed windows 141 are formed in the gripping member, one in each arm, each window being aligned with a corresponding window 171 formed in the outer tubular sleeve member, the two pairs of windows moving together in rotational alignment. Alternatively the gripping member and/or the outer tubular sleeve member may be manufactured fully or partly from a transparent material. Each arm comprises an outer curved surface 147 adapted to engage a correspondingly curved distal actuation edge 177 of the outer tubular sleeve member 170, as well as a pair of inclined edge portions 146 adapted to engage a pair of corresponding inclined actuation surfaces 176. By this arrangement the inclined actuation surfaces 176 will force the gripping shoulders outwardly to their open position as the inclined edge portions 146 are moved distally and into sliding contact with the actuation surfaces. Correspondingly, when the arms are moved proximally the outer curved surfaces 147 engage the actuation edges 177 and are thereby forced inwardly into their locked position.

Figure 2B:
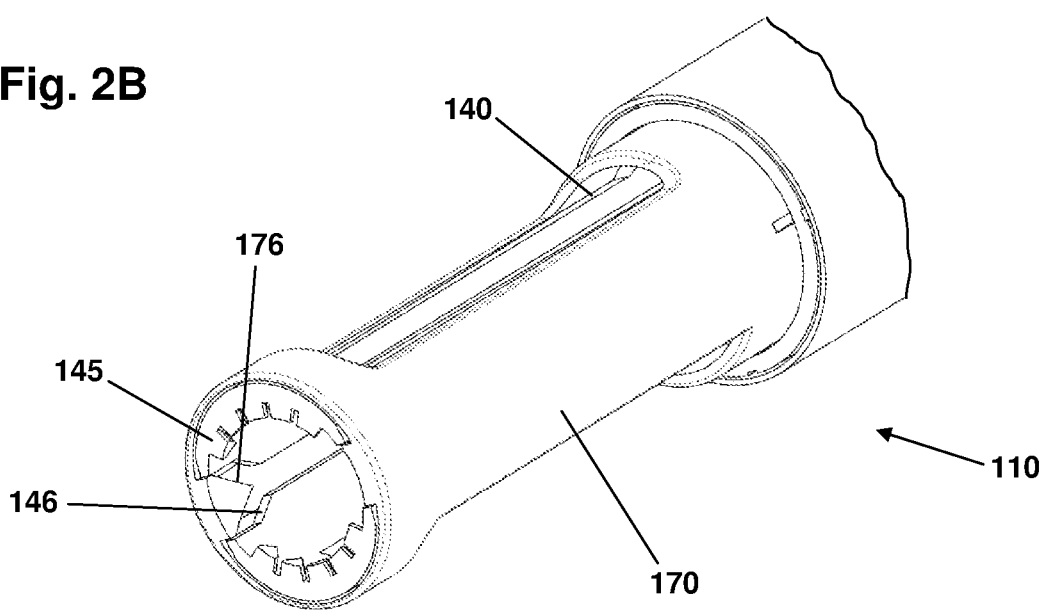
Figure 3:
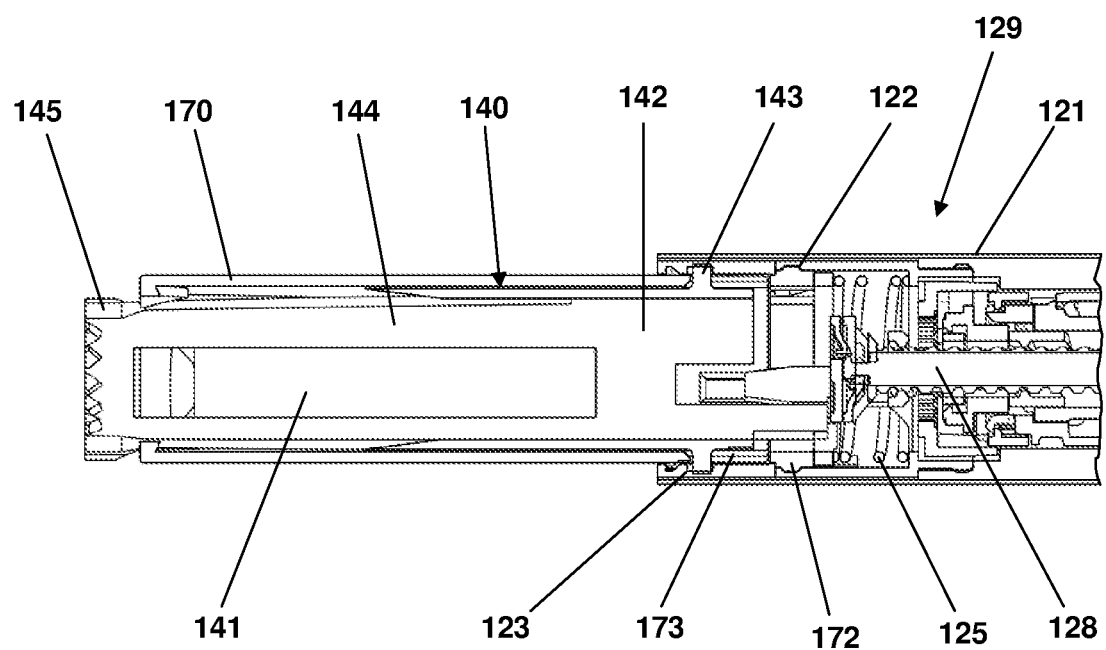
FIG. 3 shows a cross-sectional view of the cartridge holder of FIG. 2A.

FIG. 3 shows a cross-sectional view of the cartridge holder assembly and distal portion of the drive assembly portion 120 shown in FIGS. 1 and 2. As described above, the inner gripping member 140 comprising opposed arms 144 with distal gripping shoulders 145 is housed inside the outer tubular sleeve member 170. The outer sleeve member is partly arranged in the distal portion of the housing 121 and is provided with a proximal circumferential flange 172 guided in a corresponding circumferential inner groove 122 formed in the housing, this allowing the outer member to rotate relative to the housing. The outer sleeve member is further provided with two opposed proximal openings 173 allowing control protrusions 143 provided on the gripping member to engage a helical groove 123 formed in the housing portion, this engagement controlling axial movement of the inner gripping member as the outer tubular sleeve member is rotated. A spring member 125 arranged in the housing provides a distally directed biasing force on a mounted cartridge. The housing portion is further provided with a coupling mechanism 129 controlled by the rotational actuation of the cartridge holder to lock and unlock engagement between the piston rod and the drive means of the expelling mechanism. By providing a coupling mechanism controlled by rotation of the cartridge holder the mechanism can be designed to be activated after a cartridge has been locked in place and with the piston rod 128 in proper contact with a cartridge piston, this ensuring that neither an air gap is formed between the piston and the piston rod, nor that the piston is elastically deformed during the mounting procedure.

The drug delivery device of FIG. 1 may be provided with electronic means adapted to detect, store and display information in respect of one or more expelled doses of drug, e.g. in the form of an electronic module integrated in the proximal end of the device as in NovoPen Echo® from Novo Nordisk, the electronic module comprising a display arranged in the release button, see WO 2010/052275.

In the description of exemplary embodiments of the invention a drug delivery device of the general pen type has been shown, however, the drug delivery device may have other form-factors, e.g. box-formed as the Innovo® device from Novo Nordisk, and may also be provided with a motorized expelling mechanism.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A drug delivery device adapted to receive a cartridge and hold it in a mounted position, thereby providing a mounted cartridge comprising a cylindrical body portion, a distal outlet portion and an axially displaceable piston, the drug delivery device comprising:
   a housing,
   an expelling assembly comprising:
      a piston rod adapted to engage and axially displace the piston in the mounted cartridge in a distal direction to thereby expel a dose of drug from the cartridge, and
      a drive assembly adapted to move the piston rod in the distal direction corresponding to a set dose,
      an actuation member actuatable between a loading state and a mounted state,
      a coupling mechanism actuatable between:
         a resetting state in which the piston rod can be moved proximally, and
         an operational state in which the drive assembly can drive the piston rod distally but in which the piston rod cannot be moved proximally,
      wherein the coupling mechanism is actuated from the resetting state to the operational state when the actuation member is actuated from the loading state to the mounted state,
   a front-loaded cartridge holder assembly having a central axis and being adapted to receive and hold the cartridge in a mounted state, comprising:
      a distal receiving opening, and
      a cartridge holding structure actuatable between:
         a receiving state in which the cartridge can be received in a proximal direction through the distal receiving opening, and
         a holding state in which a received cartridge is held in the mounted state,
      wherein the cartridge holding structure further comprises one or more locking arms each having distal gripping portions, wherein:
         each locking arm is structured to move proximally into the distal receiving opening when the cartridge holding structure is actuated from the receiving state to the holding state, whereby each locking arm is structured to move both, radially inwards towards the central axis, and proximally, thereby being structured to grip a distally facing surface of the cartridge, when present, and
         each locking arm is structured to move distally out of the distal receiving opening when the cartridge holding structure is actuated from the holding state to the receiving state, whereby each locking arm is structured to move both radially outwards away from the central axis, and distally, thereby being structured to un-grip the distally facing surface of a cartridge, when present,
      a user operated actuation sleeve forming the actuation member and being rotationally actuatable relative to the housing between the loading state and the mounted state, wherein the actuation sleeve is actuatable from the loading state through an intermediate state to the mounted state, wherein:
         the cartridge holding structure is actuated from the receiving state to the holding state when the actuation sleeve is actuated from the loading state to the intermediate state, and
         the coupling mechanism is actuated from the resetting state to the operational state when the actuation sleeve is actuated from the intermediate state to the mounted state,
      wherein the actuation sleeve and the one or more locking arms are operationally coupled to each other such that:
         each locking arm is moved laterally and held in a lateral receiving position when the locking arm is moved distally corresponding to the receiving state, and each locking arm is moved centrally and held in a central holding position when the locking arm is moved proximally corresponding to the holding state, wherein the actuation sleeve encloses at least a portion of the mounted cartridge and extends to a distal end of the cartridge holding structure, the actuation sleeve comprising inspection structure allowing at least a portion of an enclosed cartridge portion to be visually inspected.

2. The drug delivery device as in claim 1, wherein at least one of the one or more locking arms comprises one or more openings or is at least partially transparent.

3. The drug delivery device as in claim 1, wherein the actuation sleeve comprises one or more openings or is at least partially transparent, thereby providing the inspection structure.

4. The drug delivery device as in claim 1, wherein the cartridge holding structure is rotationally coupled to the actuation sleeve.

5. The drug delivery device as in claim 1, wherein the actuation sleeve encloses a distal portion of the cartridge holding structure in the holding state.

6. The drug delivery device as in claim 1 in combination with a cartridge comprising a cylindrical body portion, a distal outlet portion and an axially displaceable piston, the cartridge being adapted to be received in and held in the mounted state in the cartridge holding structure.

7. The drug delivery device as in claim 1, wherein the actuation sleeve axially encloses at least 50% of a length of the mounted cartridge.

8. A method of operating a drug delivery system, comprising:
providing a cartridge comprising a cylindrical body portion having opposed distal and proximal portions, a distal outlet portion and an axially displaceable piston,
providing a drug delivery device comprising:
a front-loaded cartridge holder adapted to axially receive the cartridge through a distal receiving opening in a proximal direction to hold the cartridge in a mounted position, the cartridge holder being actuatable between a receiving state in which the cartridge can be received in the proximal direction through the distal receiving opening and a holding state,
the front-loaded cartridge holder further comprises one or more locking arms each having distal gripping portions, wherein:
wherein each locking arm is moved proximally into the distal receiving opening when the cartridge holder is actuated from the receiving state to the holding state, whereby each locking moving arm moves both, radially inwards towards a central axis, and proximally, thereby gripping a distally facing surface of the cartridge, when present, and
wherein each locking arm is moved distally out of the distal receiving opening when the cartridge holder is actuated from the holding state to the receiving state, whereby each locking arm moves both, radially outwards away from the central axis, and distally, thereby un-gripping the distally facing surface of the cartridge, when present,
an actuation sleeve comprising an inspection structure and the actuation sleeve being rotationally actuatable relative to the housing from a loading state through an intermediate state to a mounted state, wherein:
the actuation sleeve and the one or more locking arms are operationally coupled to each other such that:
each locking arm is moved laterally and held in a lateral receiving position when the locking arm is moved distally corresponding to the receiving state,
each locking arm is moved centrally and held in a central holding position when the locking arm is moved proximally corresponding to the holding state, and
the cartridge holder is actuated from the receiving state to the holding state when the actuation sleeve is actuated from the loading state to the intermediate state, and
a coupling mechanism is actuated from a resetting state to an operational state when the actuation sleeve is actuated from the intermediate state to the mounted state,
an expelling assembly adapted to engage and axially displace the piston in the cartridge when mounted in the drug delivery device, wherein the expelling assembly comprises the coupling mechanism, which is actuatable between:
the resetting state in which the piston rod can be moved proximally, and
the operational state in which the drive assembly can drive the piston rod distally but in which the piston rod cannot be moved proximally,
inserting the cartridge in the cartridge holder through the distal receiving opening, the actuation sleeve axially enclosing at least 50% of a cartridge length, and
rotating the actuation sleeve to actuate the cartridge holder from the receiving state to the holding state.

9. The method of operating a drug delivery system as in claim 8, further comprising:
inspecting the inserted cartridge through the actuation sleeve inspection structure.

* * * * *